(12) United States Patent
Huang et al.

(10) Patent No.: US 11,576,939 B2
(45) Date of Patent: Feb. 14, 2023

(54) METHOD FOR PRESERVING PROBIOTIC COMPOSITION AND USE THEREOF

(71) Applicant: National Kaohsiung University of Science and Technology, Kaohsiung (TW)

(72) Inventors: Ying-Tang Huang, Kaohsiung (TW); Ling-Hong Zheng, Kaohsiung (TW)

(73) Assignee: NATIONAL KAOHSIUNG UNIVERSITY OF SCIENCE AND TECHNOLOGY, Kaohsiung (TW)

( * ) Notice: Subject to any disclaimer, the term of this patent is extended or adjusted under 35 U.S.C. 154(b) by 0 days.

(21) Appl. No.: 16/930,450

(22) Filed: Jul. 16, 2020

(65) Prior Publication Data

US 2021/0015879 A1    Jan. 21, 2021

(30) Foreign Application Priority Data

Jul. 19, 2019   (TW) ................... 108125679

(51) Int. Cl.

| | |
|---|---|
| *A61K 36/064* | (2006.01) |
| *A61K 35/744* | (2015.01) |
| *A61K 35/742* | (2015.01) |
| *A61K 35/741* | (2015.01) |
| *A61K 35/745* | (2015.01) |
| *A61K 35/00* | (2006.01) |
| *A61K 39/07* | (2006.01) |
| *A61K 39/09* | (2006.01) |
| *A61K 39/104* | (2006.01) |
| *C12N 1/20* | (2006.01) |
| *A23K 10/18* | (2016.01) |
| *A23K 30/00* | (2016.01) |
| *A23L 33/135* | (2016.01) |

(52) U.S. Cl.
CPC ............ *A61K 36/064* (2013.01); *A23K 10/18* (2016.05); *A23K 30/00* (2016.05); *A23L 33/135* (2016.08); *A61K 35/741* (2013.01); *A61K 35/742* (2013.01); *A61K 35/744* (2013.01); *A61K 35/745* (2013.01); *A61K 39/07* (2013.01); *A61K 39/09* (2013.01); *A61K 39/104* (2013.01); *C12N 1/20* (2013.01); *A23V 2002/00* (2013.01); *A61K 2035/115* (2013.01)

(58) Field of Classification Search
None
See application file for complete search history.

(56) References Cited

FOREIGN PATENT DOCUMENTS

CN         101289648 A   * 10/2008

OTHER PUBLICATIONS

Machine translation of CN 101289648 A, pp. 1-13, 2008.*

* cited by examiner

*Primary Examiner* — Sarvamangala Devi
(74) *Attorney, Agent, or Firm* — WPAT, PC

(57) ABSTRACT

The present invention discloses a method for preserving a probiotic composition, including: providing a bacterial cell suspension, which is one or more bacterial cell suspensions of a bacterium or *Saccharomyces boulardii*; mixing the bacterial cell suspension with a sodium alginate solution or an alginic acid solution; and adding the mixture to a calcium ion solution until the mixture is immobilized in a shape. The technology of the present invention has the effects of long-term preservation at room temperature and resistance to high temperature, and can be applied to ordinary bacterial strains, without being limited to a small number of bacterial species able to form endospore, and without requiring the strains to be frozen for preservation. The method of the present invention can be applied to the preparation of aquatic feeds, animal feeds, or probiotics that human beings need.

6 Claims, 1 Drawing Sheet

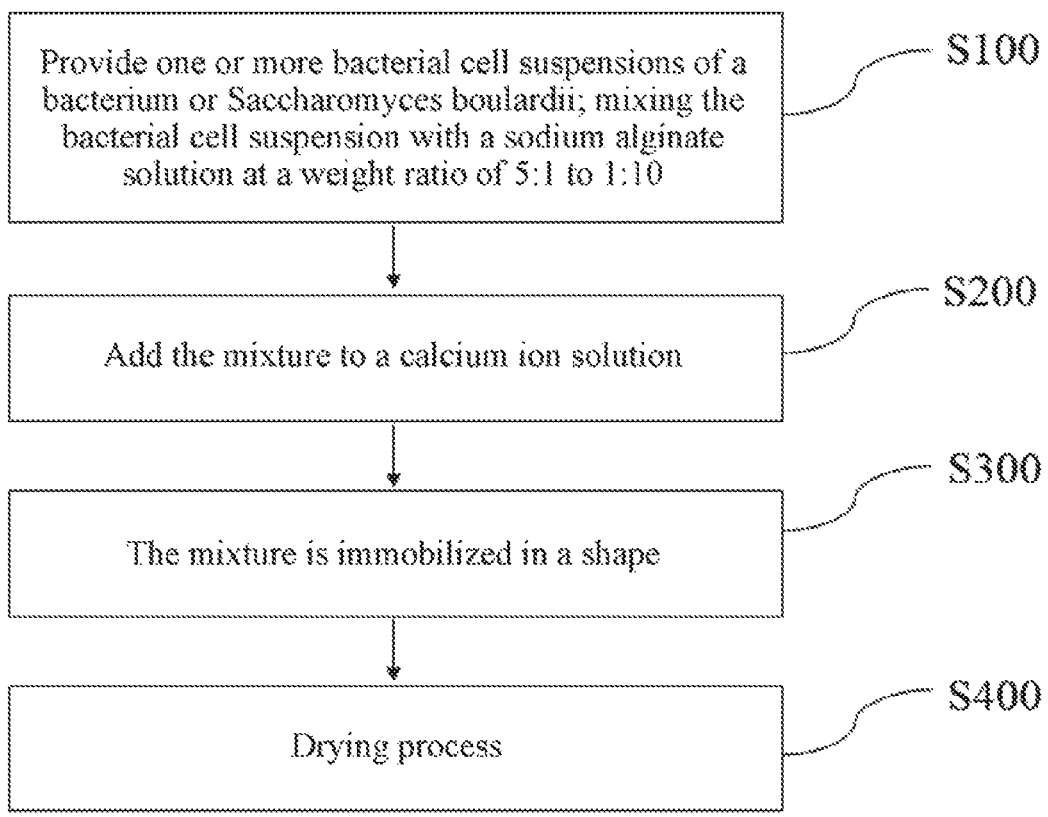

METHOD FOR PRESERVING PROBIOTIC COMPOSITION AND USE THEREOF

BACKGROUND

Technical Field

The present invention relates to a method for culturing, maintaining, or preserving microorganisms or compositions thereof, especially maintaining or preserving viable microorganisms, and also relates to the forming or preparation of an animal feed, especially through aggregation or granulation.

Related Art

Probiotics such as lactic acid bacteria can be used in the aquaculture environment to improve the growth and immunity of fish, so as to increase the yield of fish produced through aquaculture. However, there are still limitations on the practical use of probiotics. Because the probiotics are not resistant to high temperature, the probiotic strains cannot be directly added to the feed preparation process, but instead, the probiotics need to be sprayed onto the surface of the feed after the preparation of the feed is completed, which is time- and labor-consuming and increases the costs of the feed. The issue that how much of the probiotics sprayed on the surface of the feed will remain on the feed after the feed is exposed to water as well as factors such as hot outdoor environment need to be taken into consideration.

In the aquaculture environment, the excessive use of antibiotics leads to increased drug resistance of pathogenic bacteria, greatly damaging the balance of normal bacterial flora in the aquaculture water, and threatening the aquaculture production and the safety of aquatic products. To reduce harmful materials such as ammonia nitrogen and nitrite nitrogen, methods such as water changing and aeration are used during the aquaculture, but these methods have severe limitations because of short duration of efficacy and high costs.

There are two methods for long-term preservation of the probiotics at room temperature: one is causing bacteria to form endospores, which is only suitable for a small number of bacterial species; and the other is freeze drying, which requires the use of a cryoprotectant agent, but not all bacteria can be provided with a suitable cryoprotectant agent.

The feed preparation process generally requires heating to 80° C. or higher or even to 120° C. or higher. As the probiotics are not resistant to high temperature, the probiotics can be induced to form endospores and then added to the preparation process. However, only a small number of bacterial species have the ability to form endospores.

The mixture of the probiotics and alginate matrix can be microencapsulated by vegetable oil and Tween-80, and the microcapsule can only help survival of the probiotics in acid, bile, or short-time heating.

SUMMARY

Problems to be Solved by the Present Invention:

1. Problem of long-term preservation of probiotics: There are two methods for long-term preservation of the probiotics at room temperature: one is causing bacteria to form endospores, which is only suitable for a small number of bacterial species; and the other is freeze drying, which requires the use of a cryoprotectant agent, but not all bacteria can be provided with a suitable cryoprotectant agent.

2. Problem that probiotics are not resistant to high temperature: The feed preparation process requires heating to 80° C. or higher or even to 120° C. or higher. Therefore, there are two methods for adding probiotics to the feed: one is inducing the probiotics to form endospores and then added to the preparation process, but only a small number of bacterial species have the ability to form endospores; and the other is spraying the probiotics onto the surface of the feed after the preparation of the feed is completed, which is time- and labor-consuming and increases the costs of the feed.

3. Problem in aquaculture: One important factor affecting the yield of aquaculture is diseases, which cause massive losses. Therefore, antibiotics are usually used to treat diseases in the aquaculture industry, which may cause strains to evolve drug resistance. Specific drug resistance genes from the aquatic organisms can be passed on, in a special way, to human-health-related bacteria, and through the food chain, drug resistance bacteria may harm humans at the top of the food chain, causing health problems of humans. Therefore, it is necessary to look for other ways to maintain the health of aquatic organisms, and the probiotics is worth research.

To achieve the above objectives, the present invention discloses a method for preserving a probiotic composition, including: providing a bacterial cell suspension, which is one or more bacterial cell suspensions of a bacterium or *Saccharomyces boulardii*; mixing the bacterial cell suspension with a sodium alginate solution or an alginic acid solution, at a weight ratio of 5:1 to 1:10; and adding the mixture to a calcium ion solution until the mixture is immobilized in a shape.

As described above, sodium alginate or alginic acid is 1%-10% based on the weight of the solution.

As described above, calcium ion is 0.5%-5% based on the weight of the calcium ion solution.

As described above, the bacterium is *Shewanella* sp., *Pantoea* sp., *Pseudomonas* sp., photosynthetic bacteria, nitrifying bacteria, Lactic acid bacteria, *Bifidobacterium* sp., or *Bacillus* sp.

As described above, the calcium ion solution is any combination of more than one of a calcium chloride solution, a calcium lactate solution, a calcium carbonate solution, a calcium acetate solution, a calcium citrate solution, or a calcium oxalate solution.

To achieve the above objectives, the present invention also discloses a probiotic composition prepared by the above method for preserving a probiotic composition.

Also disclosed is an application of the probiotic composition as a feed, wherein the probiotic composition is prepared into particles and then added to an ordinary feed preparation process to prepare a feed.

Also disclosed is an application of the probiotic composition as an oral probiotic, wherein the probiotic composition is prepared into particles for human consumption.

Also disclosed is an application of the probiotic composition for preserving strains at room temperature, wherein strains of the probiotic composition can be preserved at room temperature of 15-35° C. for 36 months with some strains surviving.

Also disclosed is an application of the probiotic composition for preserving strains under high temperature treatment, wherein after strains of the probiotic composition are treated at 121° C. for 6 min, at 95° C. for 10 min, or at 65° C. for 24 h, there are still some strains surviving at high temperatures.

The efficacy of the present invention mainly lies in that: the related art enables only the endospore-forming probiotics of a small number of bacterial species to be preserved at room temperature for a long time and to be resistant to high temperature, and other ordinary strains need to be frozen and kept alive using suitable cryoprotectant agents; while the present invention overcomes the problems and difficulties in the related art, and can enable all bacterial strains and *Saccharomyces boulardii* to be preserved at room temperature for a long time and to be resistant to high temperature.

Generally the temperature of the aquaculture environment is high and may reach 40° C. in summer. For many strains, after they are put at room temperature, the culture will die. The probiotic composition of the present invention can be applied to not only endospore-forming bacteria, but also bacteria that do not have endospores. Additionally, by the method for preserving a probiotic composition of the present invention, probiotics not only can be preserved at room temperature for 36 months, but also can overcome the heating process of 80° C. or higher or even 120° C. or higher in the feed preparation, and do not need to be cryopreserved even in a hot outdoor environment. Therefore, compared with the related technique, by adding the probiotic composition to a feed as an additive of a living microorganism feed or making aquatic organisms eat the probiotics-containing additive of the living microorganism feed, the present invention can more effectively improve the immunity of animals or humans, adjust the intestinal function, and reduce the use of antibiotics and drugs.

BRIEF DESCRIPTION OF THE DRAWINGS

FIG. 1 is a flowchart of a method for preserving a probiotic composition of the present invention;

Table 1 shows applications of probiotics in aquaculture; and

Table 2 shows a test of the viable bacteria count released by liquid *Shewanella* sp. and dry *Shewanella* sp.

DETAILED DESCRIPTION

Feed nutrients are important factors in promoting the growth of and maintaining the health of aquatic organisms, including essential nutrients (such as energy-yielding nutrients such as proteins and amino acids, carbohydrates, lipids, and essential fatty acids), vitamins (such as vitamin A, vitamin C, and vitamin E), minerals (such as phosphorus, iron, and selenium), other non-nutrient materials such as immunostimulatory agents (such as vaccine, adjuvant, glucan, nucleotides, animal extracts, vegetable extracts, and levamisole), and probiotics.

A microorganism preparation consists of a single or mixed probiotics. Probiotics, which are living microorganisms able to improve the intestinal flora balance and health of the host, are broadly defined as living bacteria applied to humans or other animals and able to benefit the host by improving the intestinal microbial balance. Both single and mixed strains can be considered as probiotics.

Probiotics can be used as a biological agent for improving intestinal and gastric flora and enzymatic digestion, inhibiting pathogeny microorganisms, resisting the activation of mutations and cancers, and increasing immune responses by being eaten.

Probiotics in water listed in Table.1 (Martinez Cruz et al., 2012) are defined as having abilities to secret antibacterial substances beneficial to the host, compete with and repel pathogens, increase the feed efficiency, provide nutritional value, improve water quality, increase disease resistance, and so on. There are many probiotics species applicable to aquaculture at present, and studies show that specific probiotic strains can even stabilize the water quality, increase the feed conversion rate of aquatic organisms, or enhance the disease resistance.

Table 1. Applications of Probiotics in Aquaculture

Table 1. Application of Probiotics in Aquaculture

TABLE 1

| Applications of probiotics in aquaculture Table 1. Applications of probiotics in aquaculture. | | |
|---|---|---|
| Application | Identity of the probiotic | Applied to aquatic species |
| Growth promoter | *Bacillus* sp. S11 | *Penaeus monodon* |
| | *Bacillus* sp. | Catfish |
| | *Carnobacterium divergens* | *Gadus morhua* |
| | *Alteromonas* CA2 | *Crassostrea gigas* |
| | *Lactobacillus helveticus* | *Scophthalmus maximus* |
| | *Lactobacillus lactis* AR21 | *Brachionus plicatilis* |
| | *Streptococcus thermophilius* | *Scophthalmus maximus* |
| | *Streptomyces* | *Xiphophorus helleri* |
| | *L. casei* | *Poeciliopsis gracilis* |
| | *Bacillus* NL 110, *Vibrio* NE 17 | *Macrobrachium rosenbergii* |
| | *Bacillus coagulans* | *Cyprinus carpio* koi |
| Pathogen inhibitor | *Bacillus* sp. | Penaeids |
| | *Enterococcus faecium* SP 68 | *Anguilla anguilla* |
| | *L. rhamnosus* ATCC53103 | *Oncorhynchus mykiss* |
| | *Micrococcus luteus* A1-6 | *Oncorhynchus mykiss* |
| | *Pseudomonas fluorescens* | *Oncorhynchus mykiss* |
| | *P. flurorescens* AH2 | *Oncorhynchus mykiss* |
| | *Pseudomonas* sp. | *Oncorhynchus mykiss* |
| | *Roseobacter* sp. BS. 107 | Scallop larvae |
| | *Saccharomyces cerevidae, S. exiguous, Phaffia rhodozyma* | *Litopenaeus vannamei* |
| | *Vibrio alginolyticus* | Salmonids |
| | *V. fluvialis* | *Oncorhynchus mykiss* |
| | *Tetraselmis suecica* | *Salmo solar* |
| | *Carnobacterium* sp. Hg4-03 | *Hepialus gonggaensis* larvae |
| | *Lactobacillus acidophilus* | *Clarias gariepinus* |
| | *Bacillus* spp., *Enterococcus* sp. | *Farfantepenaeus brasiliensis* |
| | *Lactococcus lactis* | *Epinephelus coioides* |

TABLE 1-continued

Applications of probiotics in aquaculture
Table 1. Applications of probiotics in aquaculture.

| Application | Identity of the probiotic | Applied to aquatic species |
|---|---|---|
| Nutrient digestibility | L. helveticus | Scophthalmus maximus |
| | Bacillus NL 110, Vibrio NE 17 | Macrobrachium rosenbergii |
| | Carnobacterium sp. Hg4-03 | Hepialus gonggaensis larvae |
| | Lactobacillus acidophillus | Clarias gariepinus |
| | Shewanella putrifaciens Pdp11 | Solea senegalensis |
| Water quality | Bacillus sp. 48 | Penacus monodon |
| | Bacillus NL 110, Vibrio sp. NE 17 | Macrobrachium rosenbergii |
| | Lactobacillus acidophilus | Clarias gariepinus |
| | B. coagulans SC8168 | Pennaeus vannamei |
| | Bacillus sp., Saccharomyces sp. | Penaeus monodon |
| Stress tolerance | Lactobacillus delbrueckii | Dicentracarchus labrax |
| | Alteromonas sp. | Sparus auratus |
| | B. subtilis, L. acidophilus, S. cerevisiae | Paralichthys olivaceus |
| | L. casei | Poecilopsis gracilis |
| | Pediococcus acidilactici | Litopenaeus stylirostris |
| | Shewanella purificiens Pdp11 | Makinaki |
| Reproduction improvement | Bacillus subtilis | Poecilia reticulata, Xiphophorus maculatus |
| | L. rhamnosus | |
| | L. acidophilus, L. casei, Enterococcus faecium, Bifidobacterium thermophilum | Xiphophorus helleri |

Adding antibiotics to the feed is one of the most effective strategies for disease control in large-scale farming environments, and the administration of drugs can be used for diagnosis, prevention, or treatment of diseases.

The present invention provides a method for preserving a probiotic composition, including: providing one or more bacterial cell suspensions of a bacterium or *Saccharomyces boulardii* and a sodium alginate solution or an alginic acid solution, and mixing the bacterial cell suspension with the sodium alginate solution or the alginic acid solution at a weight ratio of 5:1 to 1:10 (S100); adding the mixture to a calcium ion solution (S200) until the mixture is immobilized in a shape (S300); and carrying out a drying process (S400).

Example 1

The present invention provides a method for preserving a probiotic composition. A bacterial cell suspension of *Saccharomyces boulardii* and a sodium alginate solution were provided. Sodium alginate was 1%-10% based on the weight of the solution, and calcium ion was 0.5%-5% based on the weight of the calcium ion solution. The bacterial cell suspension was mixed with the sodium alginate solution at a weight ratio of 2:1, and the mixture was continuously added dropwise to a calcium ion solution until the mixture was immobilized in a shape. Then a drying process was carried out.

Example 2

The present invention provides a method for preserving a probiotic composition. Bacterial cell suspensions of *Pantoea* sp., Lactic acid bacteria, and *Saccharomyces boulardii* and a sodium alginate solution were provided. The three bacterial cell suspensions were mixed, and then the mixture was mixed with the alginic acid solution at a weight ratio of 1:3. Energy-yielding nutrients (such as mineral phosphorus) and other non-nutrient materials (such as animal extracts such as fish powder, fresh and bone powder, and scallop extracts) needed for aquaculture were added to the mixture. The mixture was added dropwise to a calcium ion solution until the mixture was immobilized in a shape. Then a drying process was carried out.

In the method for preserving a probiotic composition of the present invention, sodium alginate or alginic acid is 1%-10%, preferably 1%-6%, and most preferably 1%-5% based on the weight of the solution.

In the method for preserving a probiotic composition of the present invention, calcium ion is 0.5%-5%, preferably 1%-3%, and most preferably 1.5%-2.5% based on the weight of the calcium ion solution.

Probiotics commonly used for commercial use at present include two bacteria, namely, *Lactobacillus acidophilus* and *Bifidobacterium* (also known as *Bifidus*); and *Saccharomyces boulardii* which is a species of yeast used for treating some diarrhea and infectious enteritis caused by bacteria.

The bacterial cell suspension of the present invention can be bacterial cell suspensions of all bacteria and of *Saccharomyces boulardii*. Therefore, a combination of any bacterium and *Saccharomyces boulardii* may be used, a combination of any two bacteria may be used, or a combination of any two or more bacteria and *Saccharomyces boulardii* may be used.

As described above, the bacterium is preferably *Shewanella* sp., *Pantoea* sp., *Pseudomonas* sp., photosynthetic bacteria, nitrifying bacteria, lactic acid bacteria, *Bifidobacterium* sp., *Bacillus* sp., and *Saccharomyces boulardii*.

*Shewanella* sp. are gram-negative acteria and facultative anaerobic bacteria, do not form spores, are covered with cilium, have a single flagellum, and have a length of 2-3 μm and a diameter of 0.4-0.7 μm.

In the method for preserving a probiotic composition of the present invention, the calcium ion solution is any combination of more than one of a calcium chloride solution, a calcium lactate solution, a calcium carbonate solution, a calcium acetate solution, a calcium citrate solution, or a calcium oxalate solution. Therefore, a combination of more than one calcium ion solution can be used during the process of the method for preserving a probiotic composition, so that the mixture obtained after the bacterial cell suspension is mixed with the sodium alginate solution or alginic acid solution can be immobilized in a shape after being added dropwise into the mixed calcium ion solutions. A drying process may further be carried out.

The health of the human body is closely related to the composition of intestinal probiotic flora. Different flora species are related to each other, the flora and the host are related to each other, and the flora, the host, and the environment are also related to each other. One or more species of microorganisms, when fed to humans or animals, can improve the intestinal flora quality. If the composition of flora is relatively stable, the probiotic composition of the present invention being a dominant strain can exhibit improved performance in the host.

Preferably, the calcium ion solution may be further subjected to a sterilizing process to enable the probiotic composition of the present invention to become a dominant strain in the host.

As described above, the calcium ion solution is preferably a calcium chloride solution.

Luria-Bertani broth (LB broth) is the most commonly used nutritious broth in microbiological experiments, is used for culturing bacteria such as *Escherichia coli*, and includes a liquid medium and a solid medium made by adding Agar.

Phosphate buffered saline (PBS) can maintain osmotic pressure, is non-toxic for cells, and is a commonly used buffer solution in biological study. 10 times (10×) PBS is a commonly seen method for formulating a concentrated phosphate buffered saline.

Bacterial cell suspension entrapment means that the mixture of the bacterial cell suspension and the sodium alginate solution or the alginic acid solution is added dropwise down into the calcium chloride solution under by gravity, spraying, or other common means to be immobilized into particles, or may be added dropwise to a special mold in the calcium ion solution to be immobilized in an unspecified shape, or the mixture of the bacterial cell suspension and the sodium alginate solution or the alginic acid solution may be placed in a mold first and then the mold is placed into the calcium ion solution to immobilize the mixture.

As described above, the mixture of the bacterial cell suspension and the sodium alginate solution or the alginic acid solution is preferably dropped, with the droplet size being adjusted, into the calcium ion solution to be immobilized in a shape.

As described above, the mixture of the bacterial cell suspension and the sodium alginate solution or the alginic acid solution is preferably dropped at constant speed into the calcium ion solution to be immobilized in a shape.

Example 3

In the present invention, 3% sodium alginate solution was mixed evenly with a probiotic bacterial suspension for use in aquaculture at a weight ratio of 1:2, the probiotics being *Shewanella* sp., *Pantoea* sp., *Pseudomonas* sp., Lactic acid bacteria, *Bifidobacterium* sp., yeast, or *Bacillus* sp., and the mixture was then added dropwise to 2.5% calcium chloride solution to be immobilized in a shape, and then dried and added to an ordinary feed preparation process to prepare to an aquaculture feed.

Experimental Method

*Shewanella* sp. bacterial suspension culture (1) Material Preparation:

Experimental materials: LB broth, agar, sodium alginate, calcium chloride, and PBS (10×) pH 7.4

LB broth: LB broth containing 10 g/L Tryptone, 5 g/L yeast extract, and 5 g/L NaCl was prepared by using primary water.

(2) Experimental Methods:

A single colony of *Shewanella* sp. was placed in 5 mL LB broth and shake-cultured at 37° C. for 16 hours, and then poured into 1 L LB broth, shake-cultured at 37° C. for 16 hours, and diluted by LB broth to $OD_{600}=1.8$ through spectrophotometer to obtain the bacterial cell suspension.

Probiotic Bacterial Suspension Entrapment (1) Material Preparation:

(a) Sodium alginate solution: 30 g sodium alginate was added to 1000 mL primary water.

(b) Calcium chloride solution: 25 g calcium chloride was added to 1000 mL primary water.

(2) Experimental Methods:

The bacterial cell suspension and the sodium alginate solution were mixed evenly at a weight ratio of 1:2, and then the mixture was added dropwise to the calcium chloride solution by gravity to be immobilized in a shape, dried at 37° C., and tested.

Heat Resistance Test (1) Drug Preparation:

(a) LB broth: LB broth containing 10 g/L Tryptone, 5 g/L yeast extract, and 5 g/L NaCl was prepared by using primary water.

(b) LB culture plate: 8 g LB broth was mixed with 6 g Agar, fixed to volume of 400 mL with primary water, sterilized and then poured to a petri dish for use.

(c) 1×PBS: 10×PBS (1.37 M NaCl, 0.1 M $Na_2HPO_4$, 27 mM KCl, and 18 mM $KH_2PO_4$ pH7.4) was diluted to 1× with primary water.

(2) Experimental Methods:

After dried *Shewanella* sp. were preserved at room temperature for a year, a dry bead containing bacteria formed through probiotic bacterial suspension entrapment and 1 mL bacterial cell suspension were treated at 121° C. for 6 min. The dry bead containing bacteria was then placed in 1 mL 1×PBS, respectively sampled for 100 μL at 0, 0.5, 1, 1.5, 2, 2.5, 3, 3.5, and 4 h. The samples were plated on the LB culture plate, and cultured at 37° C. for 24 hours. Then the colony counts were calculated.

*Shewanella* sp. (liquid): liquid *Shewanella* sp.

*Shewanella* sp. (dry): dry *Shewanella* sp.

Experimental Results

Samples were respectively sampled at 0, 0.5, 1, 1.5, 2, 2.5, 3, 3.5, and 4 h after treatment at 121° C. for 6 min, and there were still some surviving strains. Results are as follows:

Table 2

Table 2. Test of the viable bacteria count released by liquid *Shewanella* sp. and dry *Shewanella* sp.

TABLE 2

Test of the viable bacteria count released by liquid *Shewanella* sp. and dry *Shewanella* sp.

| Time (hour) | *Shewanella* sp. (liquid) Bacteria count/100 μl | *Shewanella* sp. (dry) Bacteria count/100 μl |
|---|---|---|
| 0 | 0 | 56 |
| 0.5 | 0 | 96 |
| 1 | 0 | 100 |
| 1.5 | 0 | 73 |
| 2 | 0 | 69 |
| 2.5 | 0 | 61 |
| 3 | 0 | 72 |
| 3.5 | 0 | 113 |
| 4 | 0 | 155 |

Example 4

According to the method for preserving a probiotic composition of the present invention, a bacterial cell suspension, which was one or more bacterial cell suspensions of a bacterium or *Saccharomyces boulardii*, was provided. The bacterial cell suspension was mixed with the sodium alginate solution or the alginic acid solution at a weight ratio of 5:1 to 1:10, and the mixture was added to a calcium ion solution to be immobilized in a shape, thus obtaining the probiotic composition of the present invention.

Example 5

The probiotic composition prepared by the method for preserving a probiotic composition of the present invention was added to an ordinary aquatic feed or animal feed preparation process to prepare a feed.

Example 6

The probiotic composition prepared by the method for preserving a probiotic composition of the present invention was added to a human food or dietary supplement for human consumption.

The experimental results of Example 3 show that strains of the probiotic composition are preserved at room temperature, where the strains of the probiotic composition can be preserved at room temperature of 15-35° C. for 36 months with some strains surviving.

The experimental results of Example 3 show that strains of the probiotic composition are preserved under high temperature treatment, where after strains of the probiotic composition are treated at 121° C. for 6 min, at 95° C. for 10 min, or at 65° C. for 24 h, there are still some strains surviving.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A probiotic composition prepared by a method comprising:
    providing a bacterial cell suspension comprising a combination of a strain of *Shewanella* sp. and a strain of *Saccharomyces boulardii*,
    mixing the bacterial cell suspension with 1% to 5% sodium alginate solution or 1% to 5% alginic acid solution at a weight ratio of 5:1 to 1:10 to obtain a mixture; and
    adding the mixture to a 1 to 3% calcium chloride solution until the mixture is immobilized into a shape; and
    carrying out a drying process.

2. The probiotic composition of claim 1, wherein the bacterial cell suspension is mixed with a 3% sodium alginate solution, wherein the weight ratio is 1:2 and the mixture is added to 2.5% calcium chloride solution.

3. The probiotic composition of claim 1, wherein the probiotic composition is for application during a preparation process of a feed.

4. The probiotic composition of claim 1, wherein the probiotic composition is for application as an oral probiotic.

5. The probiotic composition according to claim 2, wherein the strains of the probiotic composition are preserved at a room temperature of 15-35° C. for 36 months.

6. The probiotic composition according to claim 2, wherein the strains of the probiotic composition are preserved at 121° C. for 6 minutes.

* * * * *